US00PP21168P2

(12) United States Plant Patent
Macha et al.

(10) Patent No.: US PP21,168 P2
(45) Date of Patent: Jul. 20, 2010

(54) ***ILEX* PLANT NAMED 'GREMICR'**
(50) Latin Name: *Ilex vomitoria*
Varietal Denomination: Gremicr

(75) Inventors: Leon Macha, El Campo, TX (US); Scott Maxwell, El Campo, TX (US)

(73) Assignee: Greenleaf Nursery Company, Park Hill, OK (US)

( * ) Notice: Subject to any disclaimer, the term of this patent is extended or adjusted under 35 U.S.C. 154(b) by 0 days.

(21) Appl. No.: 12/386,453

(22) Filed: Apr. 17, 2009

(51) Int. Cl.
*A01H 5/00* (2006.01)

(52) U.S. Cl. ..... Plt./247
(58) Field of Classification Search ..... Plt./247
See application file for complete search history.

*Primary Examiner*—Annette H Para
(74) *Attorney, Agent, or Firm*—Penny J. Aguirre

(57) ABSTRACT

A new cultivar of *Ilex vomitoria*, 'Gremicr', characterized by its small evergreen leaves, its dwarf and compact growth habit, its slow growth rate, its ability to be readily propagated by semi-hardwood cuttings and its cold hardiness to U.S.D.A. Zone 7.

2 Drawing Sheets

Botanical classification *Ilex vomitoria.*
Variety denomination 'Gremicr'.

BACKGROUND OF THE INVENTION

The present invention relates to a new and distinct cultivar of *Ilex vomitoria* and will be referred to hereafter by its cultivar name, 'Gremicr'. 'Gremicr' is a new cultivar of dwarf yaupon holly, an evergreen shrub grown for use as a landscape plant.

The new cultivar was discovered by one of the Inventors as a naturally occurring branch mutation of a unnamed plant of *Ilex vomitoria* (not patented) that was growing in a container in a nursery in June 1999 in El Campo, Tex.

Asexual reproduction of the new cultivar was first accomplished by one of the Inventors using softwood stem cuttings in April 2002 in El Campo, Tex. The characteristics of 'Gremicr' have been determined to be stable and are reproduced true to type in successive generations.

SUMMARY OF THE INVENTION

The following traits have been repeatedly observed and represent the characteristics of the new cultivar as grown outdoors in trial beds and in containers in El Campo, Tex. These attributes in combination distinguish 'Gremicr' as a unique cultivar of *Ilex.*

1. 'Gremicr' exhibits small evergreen leaves.
2. 'Gremicr' exhibits a dwarf, compact growth habit.
3. 'Gremicr' exhibits a slow growth rate.
4. 'Gremicr' is readily propagated by semi-hardwood cuttings.
5. 'Gremicr' is hardy to U.S.D.A Zone 7.

'Gremicr' can be most closely compared the parent species, *Ilex vomitoria.* 'Gremicr' differs in having smaller leaves, a slower growing growth rate, a more compact plant habit, and in maturing into a smaller sized plant. 'Gremicr' may also be compared to 'Condeaux' (U.S. Plant Pat. No. 8,779), which has a similar low growing and globed-shaped plant habit. 'Gremicr' differs from 'Condeaux' in having smaller leaves that are lighter green in color, a slower growth rate, and reaching a smaller plant size at maturity. 'Gremicr' may also be compared to the cultivar 'Nana', (not patented). 'Gremicr' is similar by having a short, rounded, growth habit, however 'Gremicr' differs from 'Condeaux' in having smaller leaves, a slower growth-rate, and reaching a smaller size at maturity.

BRIEF DESCRIPTION OF THE DRAWING

The accompanying colored photographs illustrate the overall appearance and distinct characteristics of 5 year-old plants of the new *Ilex* as grown outdoors in 7-gallon containers in El Campo, Tex. The photograph in FIG. 1 is a side view and illustrates the overall appearance of 'Gremier'. The photograph in FIG. 2 provides a close-up view of the newly emerging foliage of 'Gremicr' and the photograph in FIG. 3 provides a close-up view of the mature foliage of 'Gremicr'. The colors in the photographs may differ slightly from the color values cited in the detailed botanical description, which accurately describe the colors of the new *Ilex.*

DETAILED BOTANICAL DESCRIPTION

Figure 1:
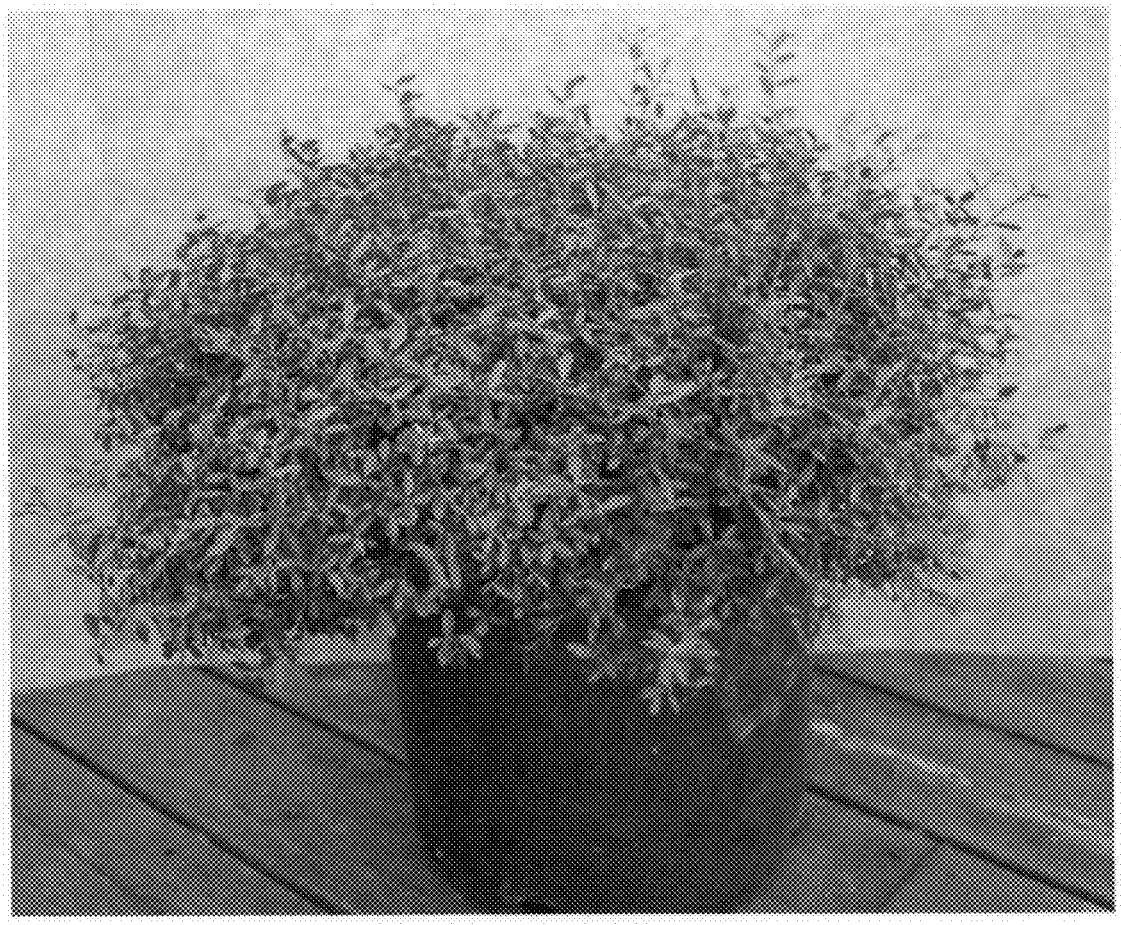
Figure 2:
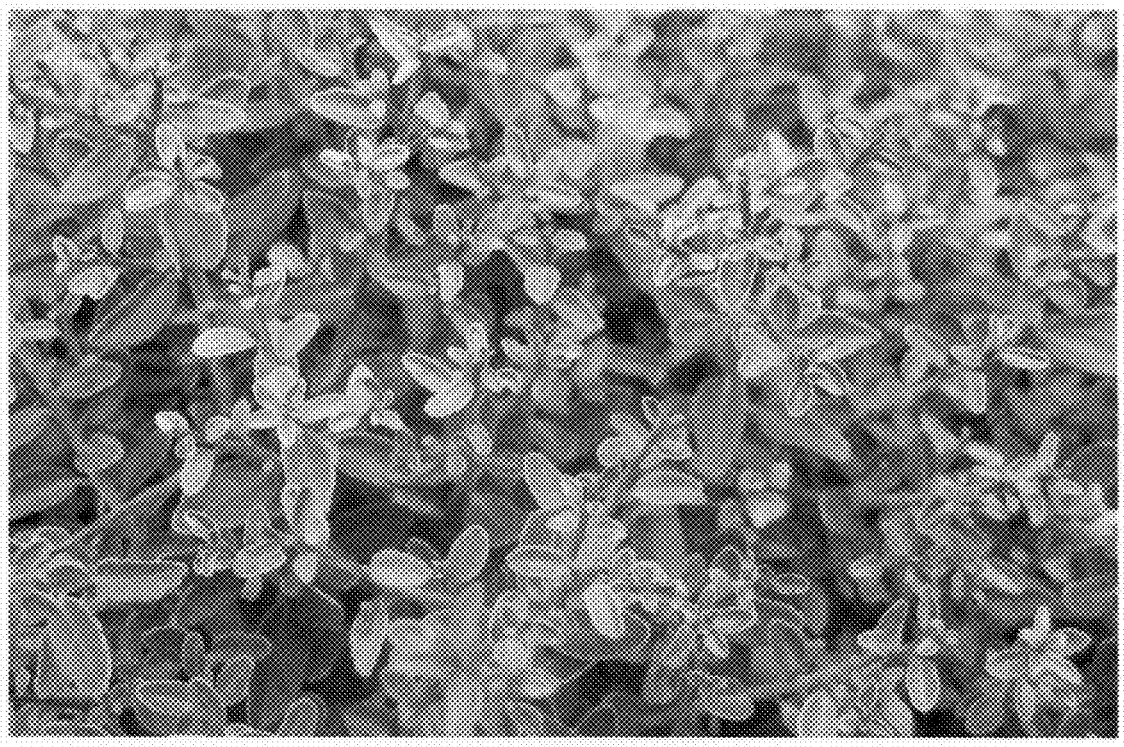
Figure 3:
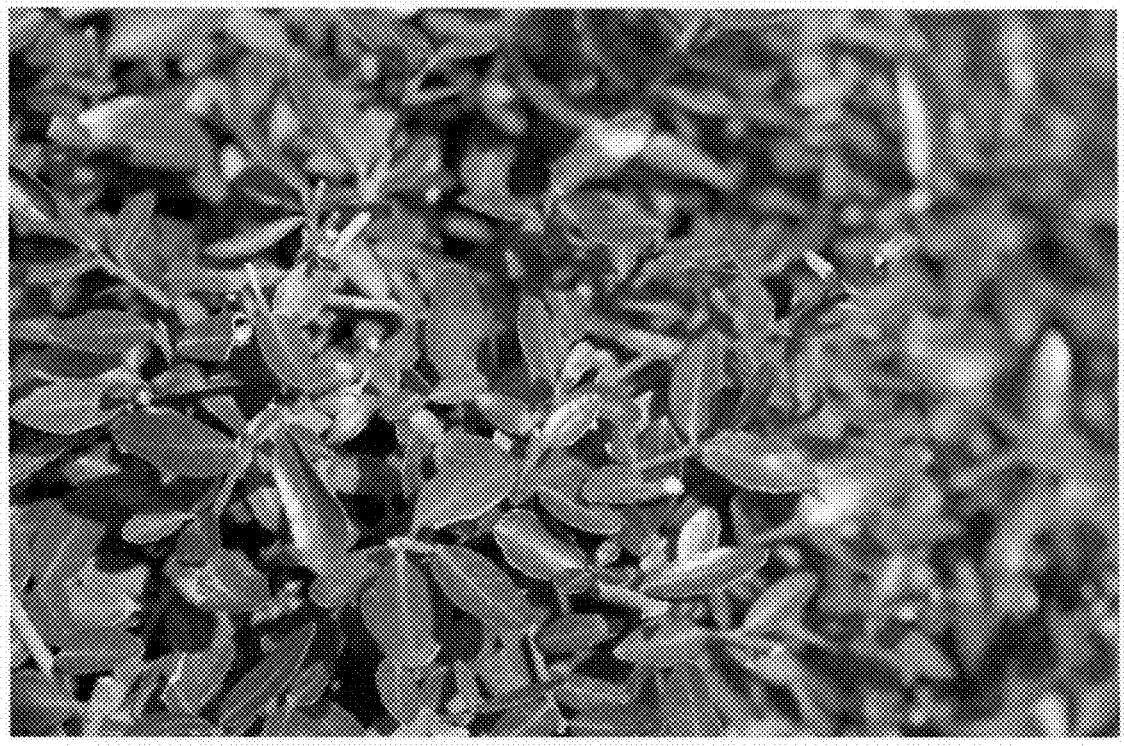

The following is a detailed description of 5 year-old plants of the new cultivar as grown outdoors in 7-gallon containers in El Campo, Tex. The phenotype of the new cultivar may vary with variations in environmental, climatic, and cultural conditions, as it has not been tested under all possible environmental conditions. The color determination is in accordance with The 2001 RHS Colour Chart of the Royal Horticultural Society, London, England, except where general color terms of ordinary dictionary significance are used.

General Description:

*Blooming period.*—Flowering not observed.
*Plant type.*—Evergreen, perennial shrub.
*Plant habit.*—Compact, dense, mounding.
*Height and spread.*—Reaches about 24 cm in height and 50 cm in width as grown in a 7-gallon container.
*Cold Hardiness.*—U.S.D.A. Zone 7.
*Diseases resistance.*—No susceptibility or resistance to diseases or pests has been observed.
*Root description.*—Fibrous.

Growth and Propagation:

*Propagation.*—Semi-hardwood stem cuttings.
*Root development.*—Semi-hardwood cuttings develop callus in about 3 months, root initiation occurs in about 4 months at 25° C. in propagation trays under greenhouse conditions without supplemental lighting, cuttings are fully rooted in 8 to 9 months in 24-cell trays at 25° C. under greenhouse conditions without supplemental lighting.

*Growth rate.*—Slow.

Stem Description:

*Shape.*—Round.

*Stem color.*—New growth emerges 144A with growing tips N79C, mature wood 199D.

*Stem size.*—Main stems; average of 1 cm in diameter, lateral branches; an average of 30 cm in length and 3 mm in width, secondary lateral branches; an average of 16 cm in length and 2.5 mm in width.

*Stem surface.*—Glabrous on new growth, becoming woody with smooth bark with a few fissures.

*Internode length.*—Lateral branches; an average of 2 cm.

*Branching.*—Densely branched; 5 to 6 main branches, with numerous secondary branches, branches are formed freely if pinched.

Foliage Description:

*Leaf shape.*—Elliptic.

*Leaf division.*—Simple.

*Leaf base.*—Cuneate.

*Leaf apex.*—Acute.

*Leaf fragrance.*—None.

*Leaf venation.*—Even-pinnate, midrib is somewhat conspicuous on upper surface only, 137C in color, all other veins match leaf color.

*Leaf margins.*—Serrulate, 5 to 6 per side on leaf 1.4 cm in length.

*Leaf arrangement.*—Alternate.

*Leaf aspect.*—Held horizontal.

*Leaf attachment.*—Petiolate.

*Leaf surface.*—Glabrous on upper surface and lower surface.

*Leaf size.*—Average of 1.4 cm in length and 6 mm in width when mature.

*Leaf quantity.*—Numerous, average of 25 per stem 13 cm in length.

*Leaf internode length.*—Average of 4 mm.

*Leaf color.*—Newly expanding leaves; 144A on upper surface and 144B on lower surface and initially heavily suffused with N79B to N79C, mature leaves; 137A on upper surface and 137C on lower surface.

*Petioles.*—An average of 3 mm in length and 1 mm in width, held at about a 45° angle, 138B in color on mature leaves, glabrous surface.

*Stipels and stipules.*—Not present.

*Flower description.*—No blooms have been observed to date.

*Seed.*—Fruit and seed production not observed to date.

It is claimed:

1. A new and distinct cultivar of *Ilex* plant named 'Gremicr' as herein illustrated and described.

* * * * *